United States Patent
Veasey et al.

(10) Patent No.: US 9,352,098 B2
(45) Date of Patent: May 31, 2016

(54) DRIVE MECHANISM FOR A DRUG DELIVERY DEVICE

(75) Inventors: Robert Veasey, Leamington Spa (GB); Simon Lewis Bilton, Leamington Spa (GB); Christopher Jones, Tewkesbury (GB); Garen Kouyoumjian, Leamington Spa (GB); Catherine Anne MacDonald, Ashby de la Zouch (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 1098 days.

(21) Appl. No.: 13/395,615

(22) PCT Filed: Sep. 29, 2010

(86) PCT No.: PCT/EP2010/064398
§ 371 (c)(1),
(2), (4) Date: Jul. 27, 2012

(87) PCT Pub. No.: WO2011/039207
PCT Pub. Date: Apr. 7, 2011

(65) Prior Publication Data
US 2013/0035647 A1    Feb. 7, 2013

(30) Foreign Application Priority Data
Sep. 30, 2009  (EP) .................... 09171740

(51) Int. Cl.
*A61M 5/315* (2006.01)
(52) U.S. Cl.
CPC ....... *A61M 5/31541* (2013.01); *A61M 5/31543* (2013.01); *A61M 5/31555* (2013.01); *A61M 5/31575* (2013.01); *A61M 5/31585* (2013.01); *Y10T 74/18992* (2015.01)
(58) Field of Classification Search
CPC ............. A61M 5/2429; A61M 5/286; A61M 5/31586; A61M 5/2425; A61M 5/282; A61M 5/315
See application file for complete search history.

(56) References Cited

U.S. PATENT DOCUMENTS

| 4,973,318 A | * | 11/1990 | Holm et al. | .................. 604/208 |
| 5,112,317 A | * | 5/1992 | Michel | .......................... 604/208 |

(Continued)

FOREIGN PATENT DOCUMENTS

| DE | 10237258 B4 | 9/2006 |
| JP | 2002-503122 | 1/2002 |

(Continued)

OTHER PUBLICATIONS

Japanese Office Action for JP App. No. 2012-531375, mailed Jul. 29, 2014.

(Continued)

*Primary Examiner* — Kami A Bosworth
*Assistant Examiner* — Matthew A Engel
(74) *Attorney, Agent, or Firm* — McDonnell Boehnen Hulbert & Berghoff LLP (57) ABSTRACT

A first input member and a second input member are arranged along a first axis and coupled in such a manner that a movement of the first input member along the first axis is converted into a rotational movement of the second input member with respect to the body. A first output member and a second output member are arranged along a second axis and coupled in such a manner that a rotational movement of the first output member is converted into a movement of the second output member along the second axis with respect to the body. The second input member and the first output member are releasably rotationally coupled.

10 Claims, 4 Drawing Sheets

(56) References Cited

U.S. PATENT DOCUMENTS

| | | | |
|---|---|---|---|
| 5,279,585 A * | 1/1994 | Balkwill | 604/207 |
| 5,545,147 A * | 8/1996 | Harris | 604/209 |
| 5,643,214 A * | 7/1997 | Marshall et al. | 604/134 |
| 5,713,857 A * | 2/1998 | Grimard et al. | 604/82 |
| 5,851,197 A * | 12/1998 | Marano et al. | 604/135 |
| 6,003,736 A | 12/1999 | Ljunggren | |
| 6,068,614 A * | 5/2000 | Kimber et al. | 604/200 |
| 6,231,550 B1 | 5/2001 | Laughlin | |
| 6,899,698 B2 * | 5/2005 | Sams | A61M 5/20 604/211 |
| 7,094,221 B2 * | 8/2006 | Veasey et al. | 604/187 |
| 7,241,278 B2 * | 7/2007 | Moller | 604/211 |
| 7,427,275 B2 * | 9/2008 | DeRuntz et al. | 604/207 |
| 7,481,977 B2 * | 1/2009 | Percival et al. | 422/64 |
| 7,850,662 B2 * | 12/2010 | Veasey et al. | 604/207 |
| 7,918,833 B2 * | 4/2011 | Veasey et al. | 604/209 |
| 7,935,088 B2 * | 5/2011 | Veasey et al. | 604/207 |
| 7,985,201 B2 * | 7/2011 | Langley et al. | 604/131 |
| 8,257,319 B2 * | 9/2012 | Plumptre | 604/211 |
| 2003/0050609 A1 * | 3/2003 | Sams | A61M 5/20 604/208 |
| 2004/0176729 A1 | 9/2004 | Langley et al. | |
| 2004/0249348 A1 * | 12/2004 | Wimpenny et al. | 604/207 |
| 2004/0260247 A1 * | 12/2004 | Veasey et al. | 604/207 |
| 2005/0033244 A1 * | 2/2005 | Veasey et al. | 604/211 |
| 2006/0264839 A1 * | 11/2006 | Veasey et al. | 604/209 |
| 2008/0027397 A1 * | 1/2008 | DeRuntz et al. | 604/220 |
| 2008/0065026 A1 | 3/2008 | Moller | |
| 2009/0198193 A1 * | 8/2009 | Veasey et al. | 604/207 |
| 2009/0264828 A1 * | 10/2009 | Dette et al. | 604/189 |
| 2010/0094205 A1 * | 4/2010 | Boyd et al. | 604/68 |
| 2010/0094206 A1 * | 4/2010 | Boyd et al. | 604/68 |
| 2010/0094207 A1 * | 4/2010 | Boyd et al. | 604/68 |
| 2010/0094253 A1 * | 4/2010 | Boyd et al. | 604/506 |
| 2010/0137792 A1 * | 6/2010 | Boyd et al. | 604/68 |
| 2010/0324494 A1 * | 12/2010 | Plumptre | 604/207 |
| 2010/0324496 A1 * | 12/2010 | Plumptre et al. | 604/207 |
| 2010/0324497 A1 * | 12/2010 | Plumptre | 604/207 |
| 2010/0324527 A1 * | 12/2010 | Plumptre | 604/500 |
| 2010/0331788 A1 * | 12/2010 | Plumptre et al. | 604/207 |
| 2010/0331790 A1 * | 12/2010 | Plumptre | 604/207 |
| 2010/0331791 A1 * | 12/2010 | Plumptre | 604/207 |
| 2010/0331792 A1 * | 12/2010 | Plumptre | 604/207 |
| 2010/0331806 A1 * | 12/2010 | Plumptre et al. | 604/500 |
| 2011/0152784 A1 * | 6/2011 | Veasey et al. | 604/207 |
| 2012/0010575 A1 * | 1/2012 | Jones et al. | 604/211 |
| 2012/0022462 A1 * | 1/2012 | Plumptre | 604/197 |
| 2012/0046643 A1 * | 2/2012 | Plumptre et al. | 604/506 |
| 2012/0089098 A1 * | 4/2012 | Boyd et al. | 604/189 |
| 2012/0089100 A1 * | 4/2012 | Veasey et al. | 604/209 |
| 2012/0283652 A1 * | 11/2012 | MacDonald et al. | 604/211 |
| 2012/0283654 A1 * | 11/2012 | MacDonald et al. | 604/211 |
| 2012/0283658 A1 * | 11/2012 | Plumptre et al. | 604/211 |
| 2012/0283662 A1 * | 11/2012 | MacDonald et al. | 604/236 |
| 2013/0030409 A1 * | 1/2013 | Macdonald et al. | 604/506 |
| 2013/0112521 A1 * | 5/2013 | Ekman | A61M 5/20 192/69.8 |
| 2013/0123710 A1 * | 5/2013 | Ekman | A61M 5/2033 604/198 |
| 2013/0274676 A1 * | 10/2013 | Ekman | A61M 5/2033 604/197 |

FOREIGN PATENT DOCUMENTS

| | | |
|---|---|---|
| JP | 2004-524117 | 8/2004 |
| RU | 2270698 C2 | 2/2006 |
| WO | 01/72361 | 10/2001 |
| WO | 03080160 A1 | 10/2003 |
| WO | WO 03/080160 * | 10/2003 |
| WO | 2007104697 A2 | 9/2007 |
| WO | 2008101829 A1 | 8/2008 |

OTHER PUBLICATIONS

English Translation of Decision on Grant Patent for Invention for Russian Patent Application No. 2012117616/14 dated Oct. 17, 2014.
Form PCT/IPEA/416, Notification of Transmittal of the International Preliminary Report on Patentability, Published Jan. 4, 2012.

* cited by examiner

DRIVE MECHANISM FOR A DRUG DELIVERY DEVICE

CROSS REFERENCE TO RELATED APPLICATIONS

The present application is a 35 U.S.C. 371 National Application of PCT/EP2010/064398 filed Sep. 29, 2010, which claims priority to European Patent Application No. 09171740.5, filed Sep. 30, 2009, the entire contents of which are incorporated entirely herein by reference.

The present invention relates to a drive mechanism for a drug delivery device and to a drug delivery device comprising the drive mechanism.

Portable drug delivery devices are used for the administration of a drug that is suitable for self-administration by a patient. A drug delivery device is especially useful in the shape of a pen, which can be handled easily and kept everywhere available.

A type of drug delivery device is constructed to be refillable and reusable many times. A drug is delivered by means of a drive mechanism, which may also serve to set the dose or amount to be delivered.

DE 102 37 258 B4 describes a drug delivery device in the shape of an injection pen having a drive mechanism, which allows to deliver a plurality of different prescribed doses. The drive mechanism comprises elements which are rotated relatively to one another around a common axis.

It is an object of the present invention to facilitate provision of a new drive mechanism for a drug delivery device or of a new drug delivery device.

This object is achieved by a drive mechanism according to claim 1. Further objects are achieved by variants and embodiments according to the dependent claims.

The drive mechanism for a drug delivery device comprises a body having a distal end and a proximal end, spaced apart in the direction of a first axis and a second axis that is parallel to the first axis. A first input member and a second input member are arranged within the body along the first axis and coupled in such a manner that a movement of the first input member along the first axis is converted into a rotational movement of the second input member with respect to the body. A first output member and a second output member are arranged within the body along the second axis and coupled in such a manner that a rotational movement of the first output member is converted into a movement of the second output member along the second axis with respect to the body. The second input member and the first output member are releasably rotationally coupled.

The body can be any housing or any component that forms part of a housing, for example. The body can also be some kind of an insert connected with an exterior housing. The body may be designed to enable the safe, correct, and/or easy handling of the device and/or to protect it from harmful liquids, dust or dirt. The body can be unitary or a multipart component of tubular or non-tubular shape. The body may house a cartridge, from which doses of a drug can be dispensed. The body can especially have the shape of an injection pen.

The term "distal end" refers to a part of the body or housing which is intended to be arranged at a portion of the drug delivery device from which a drug is dispensed. The term "proximal end" refers to a part of the body or housing which is remote from the distal end. The term "distal direction" refers to a movement in the same direction as a movement from the proximal end towards the distal end, not specifying a point of departure nor an end point, so that the movement may go beyond the distal end. The term "proximal direction" refers to a movement in the direction opposite to the distal direction.

The drive mechanism can be used to expel a drug from a receptacle or cartridge inserted in the body of a drug delivery device. The drug delivery device can be a disposable or reusable device designed to dispense a dose of a drug, especially a liquid, which may be insulin, a growth hormone, a heparin, or an analogue and/or a derivative thereof, for example. The drug may be administered by a needle, or the device may be needle-free. The device may be further designed to monitor physiological properties like blood glucose levels, for example. Each time the second output member is shifted in the distal direction with respect to the body, a dose of the drug is expelled from the drug delivery device.

In an embodiment of the drive mechanism, a shift of the first input member in the distal direction produces a shift of the second output member in the distal direction.

In a further embodiment, the second input member and the first output member are rotationally coupled when the first input member is moved in the distal direction.

In a further embodiment, a pinion member releasably rotationally couples the second input member and the first output member. A pawl member engaging with the pinion member allows rotation of the pinion member in only one direction. A clutch couples the second input member with the pinion member in a releasable fashion.

In a further embodiment, the clutch couples the second input member with the pinion member when a force is exerted on the first input member in the distal direction, and the second input member and the pinion member are not coupled when the first input member is being shifted in the proximal direction.

In a further embodiment, the pinion member has notches, and the pawl is a hinged tongue or a resilient or resiliently mounted cantilever. The pawl has a tip or edge that engages the notches, thus preventing rotation of the pinion member in one direction.

In a further embodiment, a set operation is performed by shifting the first input member in the proximal direction.

In a further embodiment, a dispense operation is performed by shifting the first input member in the distal direction.

In a further embodiment, the first input member is an input shaft, the input shaft being axially movable relatively to the body, and the second input member is an input sleeve, the input sleeve being rotatable around the first axis relatively to the body. The first output member is an output sleeve, the output sleeve being rotatable around the second axis relatively to the body, and the second output member is an output shaft, the output shaft being axially movable relatively to the body.

In a further embodiment, a last-dose nut is arranged within the body, the last-dose nut being movable relatively to the body along the first axis and being rotationally coupled with the first output member. The last-dose nut and the second input member are coupled by a screw thread, which generates a movement of the last-dose nut in either the distal or the proximal direction when a rotation of the second input member is generated by a shift of the first input member in the proximal direction. The body, the first output member or the second input member are provided with a stop element limiting the movement of the last-dose nut in the distal or the proximal direction.

In a further embodiment, the drive mechanism is provided for a fixed-dose drug delivery device.

In a further embodiment, the body or the second input member is provided with a stop element, the stop element limiting the movement of the first input member in the proximal direction.

In a further embodiment, a groove or track of the body is provided to lock the second output member rotationally to the body and to guide a shift or helical movement of the second output member along the second axis.

A drug delivery device comprising an embodiment of the drive mechanism may further comprise a compartment provided for a cartridge containing a drug and a piston that is provided to expel the drug from the cartridge, the piston being driven in the distal direction by the second output member.

An embodiment of the drive mechanism and its operation are described in the following as an example. A first output member of the drive mechanism is formed by an output sleeve, and a second output member is formed by an output shaft. The first output member is rotated by means of the input drive feature. The drive feature can comprise a first input member, formed by an input shaft, and a second input member, formed by an input sleeve. The input members are arranged along a first axis, and the output members are arranged along a second axis, parallel to the first axis. The input members and the output members are coupled by a kind of gear, which allows a unidirectional rotation of the output members. This can be achieved by an arrangement of a pinion member and a pawl member functioning in the manner of a ratchet. The pawl can be released from the pinion so that the output members are free to rotate in both directions. A clutch coupling the first input member and the second input member is provided to enable the user to set a dose without rotating the output members and to deliver a dose of the drug while the clutch is engaged and an output member rotates simultaneously with the second input member. To set a dose, the first input member is axially pulled and not rotated with respect to the body.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N -palmitoyl-des(B30) human insulin; B29-N-myristoyl human insulin; B29-N-palmitoyl human insulin; B28-N-myristoyl LysB28ProB29 human insulin; B28-N-palmitoyl -LysB28ProB29 human insulin; B30-N-myristoyl-ThrB29LysB30 human insulin; B30-N -palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu- Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCL or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

In the following, examples and embodiments of the drive mechanism are described in detail in conjunction with the appended figures.

Figure 1:
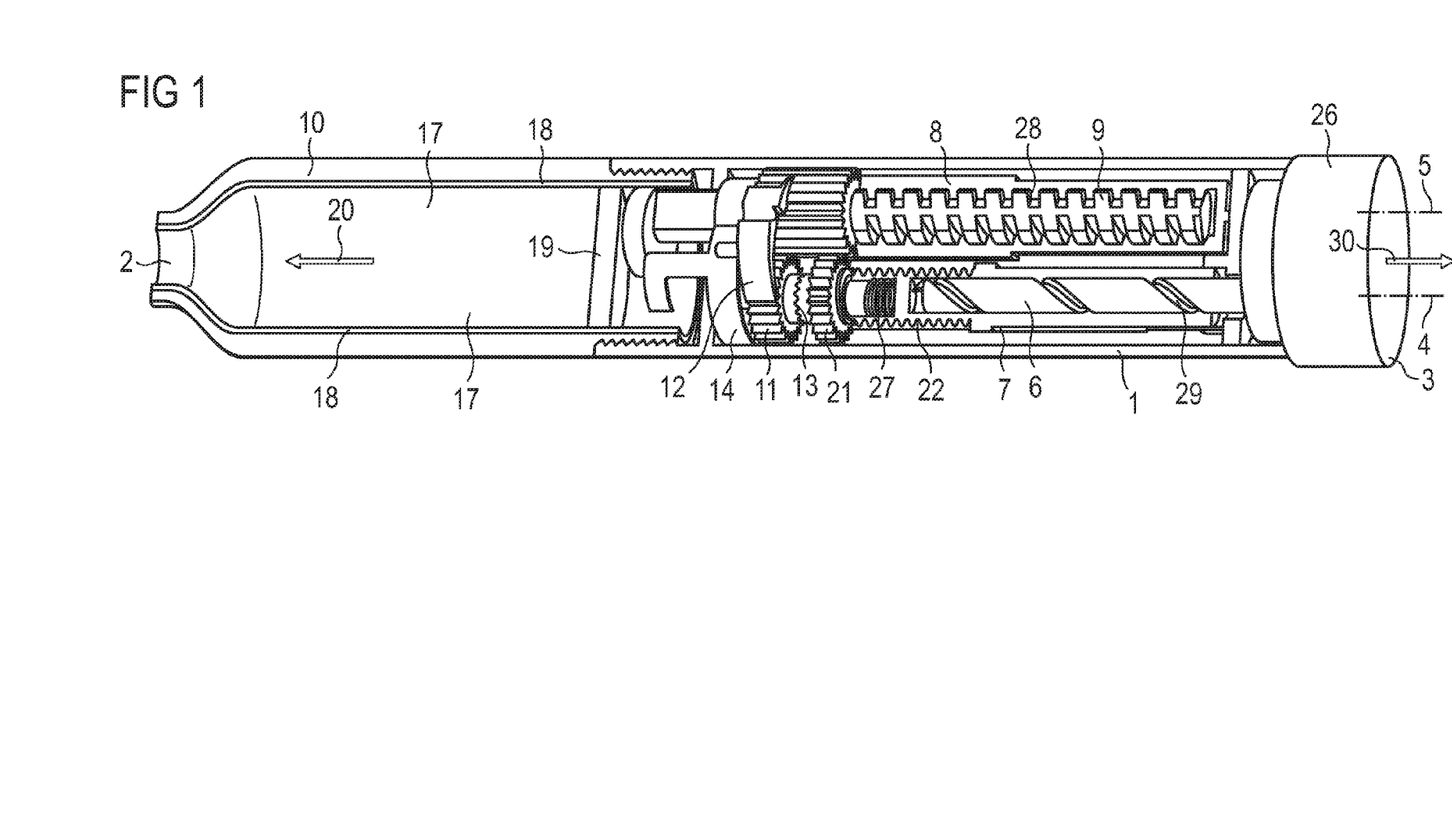
FIG. 1 shows a perspective cut-away view of an injection pen comprising an embodiment of the drive mechanism.

FIG. 1 shows a cross-section of an injection pen comprising a drive mechanism having input and output members. The body 1 has a distal end 2 and a proximal end 3. Input members of the drive mechanism are arranged along a first axis 4. Output members of the drive mechanism are arranged along a second axis 5, which is parallel to the first axis 4. A first input member 6 is formed by a shaft in this embodiment. The first input member 6 is coupled with a second input member 7, which is an input sleeve in this embodiment. The first input member 6 and the second input member 7 form an input drive feature of the drive mechanism. The coupling of the first input member 6 and the second input member 7 can be achieved by a screw thread 29. The first input member 6 is provided for an operation by the user and juts out of the body 1 at its proximal end 3. There, the first input member 6 is preferably provided with a grip 26, which can be used to pull the first input member 6 out of the body 1 in the proximal direction 30. The screw thread 29 coupling the first input member 6 with the second input member 7 makes the second input member 7, formed by the input sleeve, rotate with respect to the first input member 6 around the first axis 4 and thus relatively to the body 1. An axial movement of the second input member 7 in the distal direction or in the proximal direction is inhibited by suitable components of the drive mechanism or the body 1, like protruding elements, webs or the like. The second input member 7 therefore stays at its position and merely rotates around the first axis 4.

The second input member 7 is coupled with the first output member 8 by means of a unidirectional gear like a ratchet. The gear comprises a pinion member 11 and a pawl member 12. The pawl member 12 can be a hinged tongue or a kind of cantilever having a hook or edge engaging notches in a toothed circumference of the pinion member 11, for example. The pinion member 11 is coupled with the second input member 7 by means of a clutch 13, so that the pinion member 11 can be released from the second input member 7 to prevent the pinion member 11 from rotating simultaneously with the second input member 7. A clutch spring 27 can be provided to disengage the clutch 13 as long as the first input member 6 is not pushed in the distal direction 20. Therefore, the pinion member 11 does not rotate together with the second input member 7 when the first input member 6 is shifted in the proximal direction 30. Only when the first input member 6 is pushed in the distal direction 20 and the clutch spring 27 is compressed, the clutch 13 engages, and the pinion member 11 rotates according to the rotation of the second input member 7. Then, the pinion member 11 drives the first output member 8, which can be coupled to the pinion member 11 by means of a gear wheel forming an integral part of the first output member 8 or by means of a similar device. The pawl member 12 allows the rotation of the pinion member 11 in one rotational direction only, and consequently the rotation of the first output member 8 is restricted to the corresponding rotational direction according to the coupling between the pinion member 11 and the first output member 8.

A second output member 9 is coupled with the first output member 8. The coupling can be achieved by a further screw thread 28, for example. The first output member 8 can be an output sleeve, and the second output member 9 can be an output shaft. The coupling between the first output member 8 and the second output member 9 is such that the rotation of the first output member 8 allowed by the pawl member 12 drives the second output member 9 in the distal direction 20. The second output member 9 can be used as a piston rod or plunger driving a piston 19 in the distal direction 20. The piston 19 is provided to expel a drug from a receptacle, particularly from a cartridge 18, which is inserted in a dedicated compartment 17 at the distal end 2 of the body 1. If the body 1 is provided with a removable and attachable part 10 at its distal end 2, the cartridge 18 can be removed and exchanged with a new one, and the device can easily be refilled. This enables the drug delivery device to be reused.

After a cartridge 18 has been emptied, the removable and attachable part 10 is removed from the body 1 and the empty cartridge 18 taken out of the compartment 17. The second output member 9 has to be shifted back to its initial position near the proximal end 3 of the body 1, before a full cartridge 18 comprising a piston 19 at a proximal position can be inserted. The first output member 8 is not shifted axially with respect to the body 1, and the second output member 9 is therefore shifted relatively to the first output member 8. Because of the coupling between the first output member 8 and the second output member 9, by means of the screw thread 28 for instance, the shift of the second output member 9 in the proximal direction 30 is accompanied with the rotation of the first output member 8 in the rotational direction that is not allowed by the pinion member 11 and the engaged pawl member 12. To make the shift of the second output member 9 possible, the pawl member 12 is disengaged from the pinion member 11, so that the pinion member 11 is free to rotate in both rotational directions.

A resilient element 14 can be provided to drive the pawl member 12 out of its engagement with the pinion member 11, when the removable and attachable part 10 is removed and the unidirectional gear is thus released. When the removable and attachable part 10 is attached, the resilient element 14 is restrained from its action on the pawl member 12. The pawl member 12 is preferably also resilient or at least resiliently mounted, so that the pawl member 12 is automatically re-engaged with the pinion member 11, when the removable and attachable part 10 is attached. This enables a reset operation to be performed after the removal of an emptied cartridge. The operation of the drive mechanism will now be described with reference to FIGS. 2 to 8.

Figure 2:
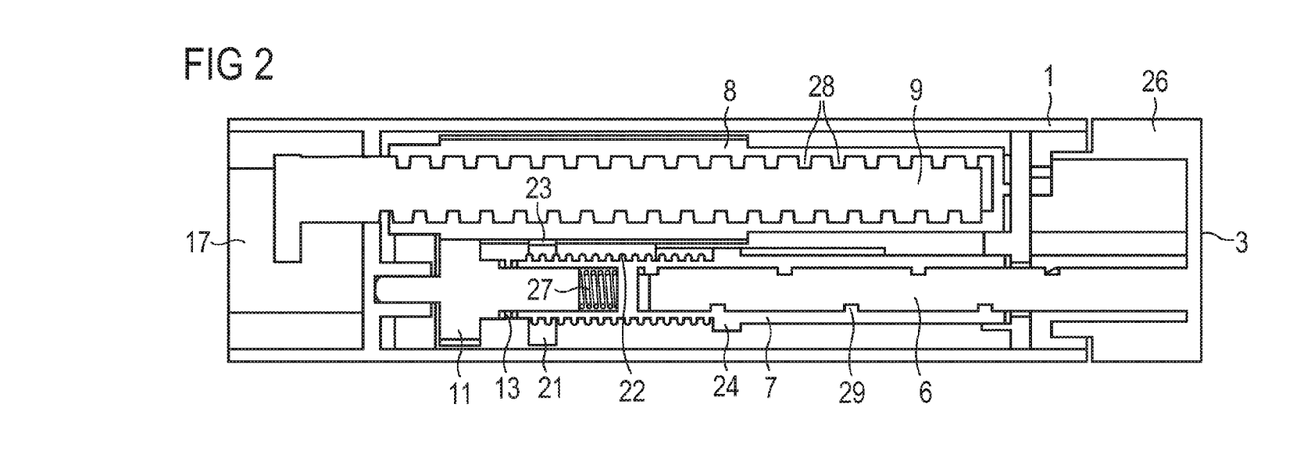
FIG. 2 shows a cross-section of the drive mechanism in a start position.

FIG. 2 shows a schematic cross-section of the drive mechanism in an initial state. The gear coupling the input drive feature and the output members is schematically represented by the pinion member 11 shown in cross-section. The removable and attachable part is attached, and the pawl member engages with the pinion member 11, restricting the rotation to one rotational direction. In this start position, a set operation can be performed by pulling the first input member 6 in the proximal direction, i.e. to the right in FIG. 2.

Figure 3:
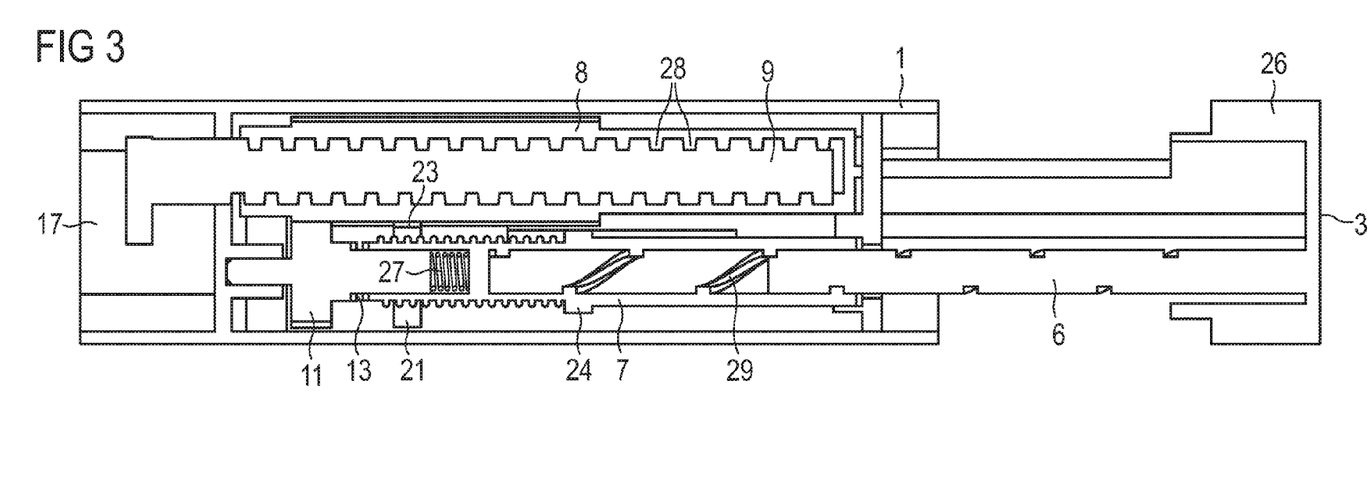
FIG. 3 shows a cross-section according to FIG. 2 after a set operation.

FIG. 3 shows a cross-section according to FIG. 2 after the set operation. The first input member 6 has been shifted in the proximal direction and sticks out of the body 1. The movement of the first input member 6 caused the second input member 7, the input sleeve, to rotate. The clutch 13 provided to couple the second input member 7 with the pinion member 11 is disengaged during the set operation. The pinion member 11 does therefore not rotate with the second input member 7. Consequently, the output members are not moved. In the state of the drive mechanism shown in FIG. 3, the set dose can be dispensed by just pushing the first input member 6 in the distal direction. This movement makes the clutch 13 engage, because the second input member 7 is pressed towards the pinion member 11 against the force of the clutch spring 27, compressing the clutch spring 27. The clutch 13 may be formed by an angular arrangement of teeth or the like. Instead of a toothed structure, the friction occurring between the surfaces of the second input member 7 and the pinion member 11, which are pressed together, may suffice to engage the pinion member 11 with the rotating second input member 7. As a result, the rotating pinion member 11 rotates the first output member 8. The coupling of the first output member 8 with the second output member 9 causes the second output member 9 to be shifted in the distal direction, thus driving the piston to expel the preset dose.

Figure 4:
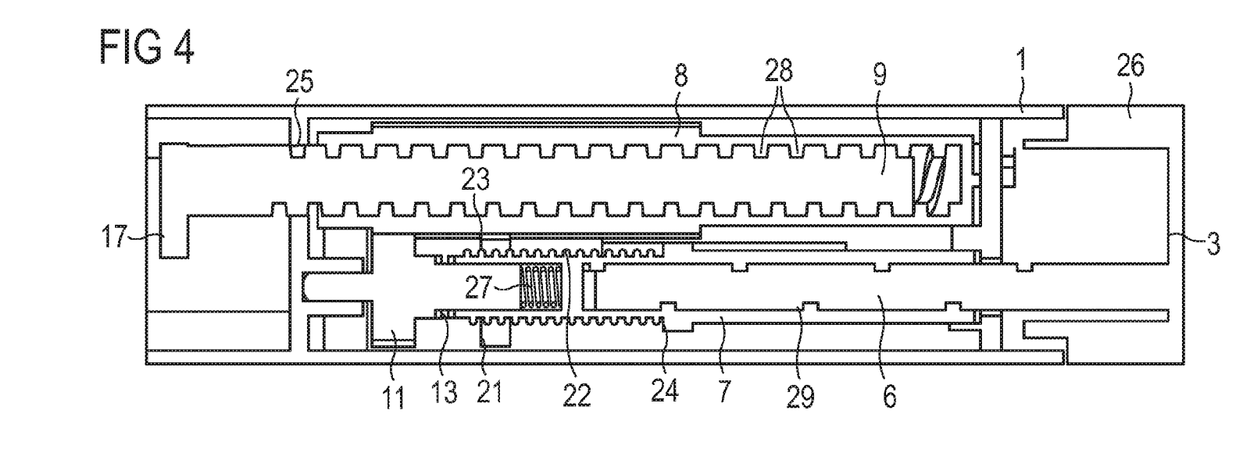
FIG. 4 shows a cross-section according to FIG. 3 after a dispense operation.

FIG. 4 shows the cross-section according to FIG. 3 after the delivery of the set dose. The state of the drive mechanism is now comparable to the initial state shown in FIG. 2, except for the second output member 9 having been shifted a small distance in the distal direction, i.e. to the left in FIG. 4. A further dose can now be set and delivered, again by moving the second output member 9 by the defined distance in the distal direction. This process can be repeated until the cartridge is empty. An axial groove or track 25 of the body 1 can be provided to lock the second output member 9 rotationally to the body 1 and allow a shift of the second output member 9 along the second axis 5 without rotation with respect to the body 1.

Figure 5:
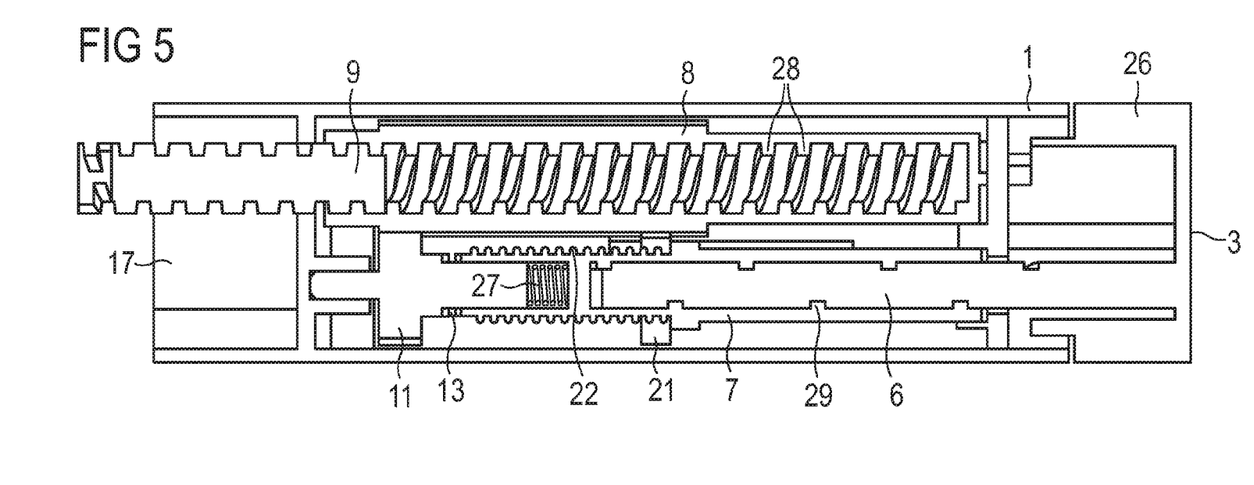
FIG. 5 shows a cross-section according to FIG. 4 after the delivery of a last dose.

FIG. 5 shows the position of the second output member 9 within the drive mechanism after the last dose of the drug has been dispensed. When the resilient element 14 is caused to disengage the pawl member 12 from the pinion member 11 by removing the removable and attachable part 10 from the main part of the body 1, the second output member 9 can be shifted in the proximal direction to its start position with the first output member 8 and the pinion member 11 freely rotating. The clutch 13 is disengaged, so that the second input member 7 does not rotate and, consequently, the first input member 6 is held stationary with respect to the body 1. In this way, the start position according to FIG. 2 is obtained.

A last-dose nut 21 may be provided to prevent the user from setting a dose when only an insufficient amount of the drug remains in the cartridge or when the cartridge is completely empty. The last-dose nut 21 is preferably in threaded engagement with the second input member 7, the input sleeve, shown by the schematically indicated screw thread 22 in FIGS. 2 to 5. The last-dose nut 21 is further in a gear tooth engagement 23 with the first output member 8, the output sleeve. During a set operation, the last-dose nut 21 advances along the input sleeve 7, in the proximal direction 30 in the example shown in the figures. This is due to the fact that the clutch 13 is not engaged during the set operation. Hence, the output sleeve 8 does not rotate and therefore, the last-dose nut 21 does not rotate either. During the dispense operation, the last-dose nut 21 does not advance relative to the input sleeve 7 in the axial direction, because the last-dose nut 21 is driven by the gear tooth engagement 23 to rotate with the output sleeve 8 at the same rotational rate as the input sleeve 7. The threads are appropriately designed to this effect.

In this operational concept, the last-dose nut 21 is moved in one direction, axially with respect to the body 1, during a set operation, while the last-dose nut 21 stays stationary in the axial direction during a dispense operation. The distance by which the last-dose nut 21 is shifted in each set operation is designed such that the last-dose nut 21 comes to a stop after the last dose has been expelled. To this purpose, the drive mechanism or the body can be provided with a stop feature, like the stop element 24, to inhibit the further movement of the last-dose nut 21 in the axial direction. As the set operation can only be performed by a movement of the input shaft 6 which makes the input sleeve 7 rotate and thus the last-dose nut 21 be shifted in the axial direction, stopping the movement of the last-dose nut 21 inhibits a shift of the input shaft 6 and thus prevents the user from setting a further dose.

Figure 6:
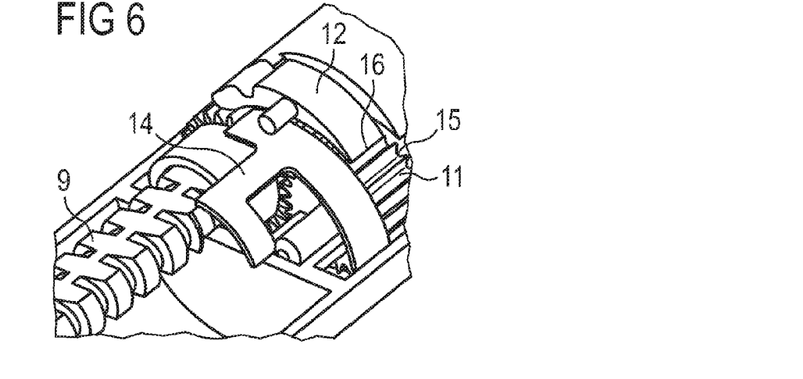
FIG. 6 shows a detail of the arrangement of the pinion member and the pawl member.

FIG. 6 shows the coupling between the drive feature and the output members by means of the pinion member 11 and the pawl member 12. The pawl member 12 is formed to be a hook or cantilever having a tip or edge 16 engaging notches 15 in the toothed pinion member 11. The resilient element 14 is kept away from the pawl member 12 by a protruding element or the like provided on the removable and attachable part 10. The pawl member 12 is therefore engaged with the pinion member 11, and a rotation of the pinion member 11 is only permitted in one rotational direction. This is the rotational direction that enables the second output member 9, the output shaft functioning as the piston rod, to be moved in the distal direction, but not be moved back in the proximal direction.

Figure 7:
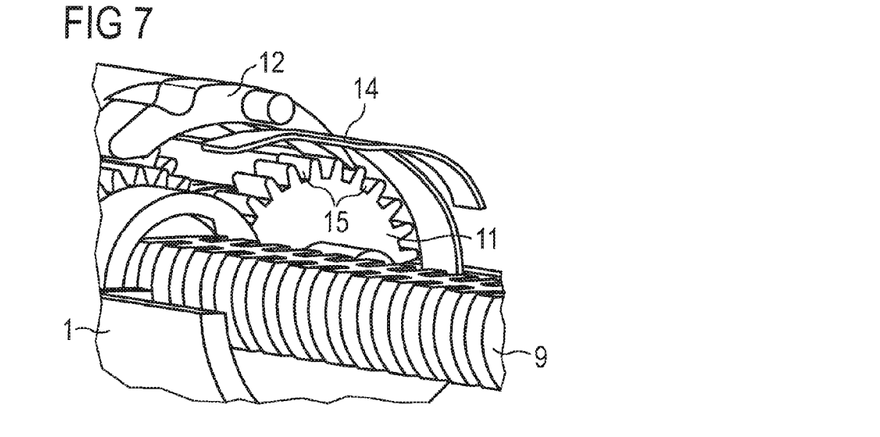
FIG. 7 shows another view of the arrangement of the pinion member with the pawl member engaged.

FIG. 7 shows the arrangement according to FIG. 6 in another perspective. The resilient element 14 is shown to be held at a distance from a protruding element of the pawl member 12. The pawl member 12 is therefore engaged with the pinion member 11. This can be achieved by the pawl member 12 being resiliently mounted. The pawl member 12 can be a plastic element, for instance, which is mounted to the drive mechanism or to the body in such a manner that the pawl member 12 occupies a position where a tip or edge 16 at the end of the pawl member 12 engages notches 15 between the teeth of the pinion member 11, when no external force is exerted on the pawl member 12.

Figure 8:
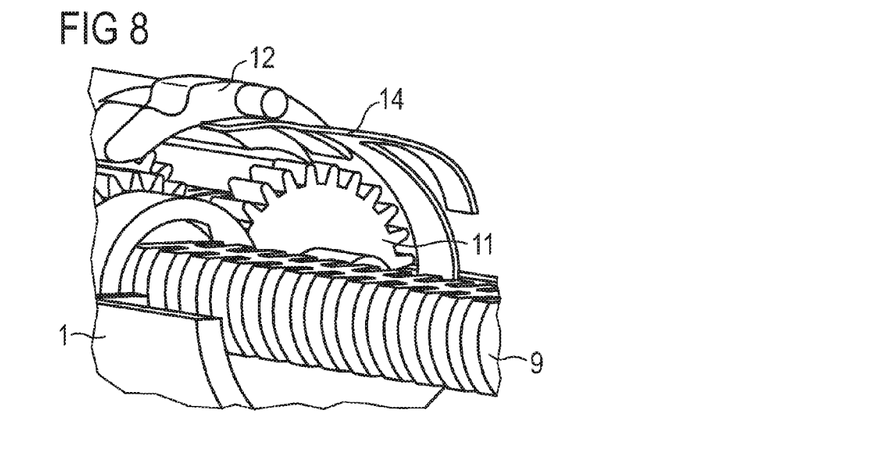
FIG. 8 shows the view according to FIG. 7 with the pawl member disengaged.

FIG. 8 shows the view according to FIG. 7 when the removable and attachable part 10 has been removed from the body 1, so that the resilient element 14 is free to relieve its tension and to come in contact with the protruding element of the pawl member 12. The resilient element 14 then pushes the pawl member 12 out of its engagement with the pinion member 11. This enables the second output member 9 to be shifted in the proximal direction, making the output sleeve 8 and the pinion member 11 rotate in the opposite rotational direction, which is now allowed by the release of the pawl member 12 from the pinion member 11.

The drive mechanism can be used in a wide range of reusable devices, particularly injection pens, and enables easy handling and an easy refill.

REFERENCE NUMERALS 1 body
2 distal end
3 proximal end
4 first axis
5 second axis
6 first input member
7 second input member
8 first output member
9 second output member
10 removable and attachable part
11 pinion member
12 pawl member
13 clutch
14 resilient element
15 notch
16 tip or edge
17 compartment
18 cartridge
19 piston
20 distal direction
21 last-dose nut
22 screw thread
23 gear tooth engagement
24 stop element
25 axial groove or track
26 grip
27 clutch spring
28 screw thread
29 screw thread
30 proximal direction

The invention claimed is:

1. A drive mechanism for a drug delivery device, comprising:
a body having a distal end and a proximal end, spaced apart in the direction of a first axis and a second axis that is parallel to the first axis,
a first input member and a second input member, arranged within the body along the first axis and coupled in such a manner that a movement of the first input member along the first axis is converted into a rotational movement of the second input member with respect to the body,
a first output member and a second output member, arranged within the body along the second axis and coupled in such a manner that a rotational movement of the first output member is converted into a movement of the second output member along the second axis with respect to the body,
the second input member and the first output member being releasably rotationally coupled when the first input member is moved in a distal direction,
a pinion member releasably rotationally coupling the second input member and the first output member,
a pawl member engaging with the pinion member allowing rotation of the pinion member in only one direction, and
a clutch coupling the second input member with the pinion member in a releasable fashion such that the clutch couples the second input member with the pinion member when a force is exerted on the first input member in the distal direction, and the second input member and the pinion member are not coupled when the first input member is being shifted in a proximal direction.

2. The drive mechanism according to claim 1, further comprising:
the pinion member having notches, the pawl member being a hinged tongue or a resilient or resiliently mounted cantilever, and the pawl member having a tip or edge that engages the notches, thus preventing rotation of the pinion member in one direction.

3. The drive mechanism according to claim 1, wherein a set operation is performed by shifting the first input member in the proximal direction.

4. The drive mechanism according to claim 1, wherein a dispense operation is performed by shifting the first input member in the distal direction.

5. The drive mechanism according to claim 1, wherein
the first input member is an input shaft, the input shaft being axially movable relatively to the body,
the second input member is an input sleeve, the input sleeve being rotatable around the first axis relatively to the body,
the first output member is an output sleeve, the output sleeve being rotatable around the second axis relatively to the body, and
the second output member is an output shaft, the output shaft being axially movable relatively to the body.

6. The drive mechanism according to claim 1, further comprising:
a last-dose nut arranged within the body, the last-dose nut being movable relatively to the body along the first axis and being rotationally coupled with the first output member,
the last-dose nut and the second input member being coupled by a screw thread,
the screw thread generating a movement of the last-dose nut in either the distal or the proximal direction when a rotation of the second input member is generated by a shift of the first input member in the proximal direction, and
the body, the first output member or the second input member being provided with a stop element limiting the movement of the last-dose nut in the distal or the proximal direction.

7. The drive mechanism according to claim 1, wherein the drive mechanism is provided for a fixed-dose drug delivery device.

8. The drive mechanism according to claim 7, further comprising:
the body or the second input member being provided with a stop element, the stop element limiting the movement of the first input member in the proximal direction.

9. The drive mechanism according to claim 1, further comprising:
a groove or track of the body locking the second output member rotationally to the body and allowing a shift of the second output member along the second axis.

10. A drug delivery device comprising a drive mechanism according to claim 1, further comprising:
a compartment provided for a cartridge containing a drug and a piston that is provided to expel the drug from the cartridge, the piston being driven in the distal direction by the second output member.

* * * * *